United States Patent
Lynch et al.

(10) Patent No.: US 11,804,304 B2
(45) Date of Patent: Oct. 31, 2023

(54) METHOD AND SOFTWARE FOR ASSESSING NEURODEVELOPMENTAL ABNORMALITIES

(71) Applicant: WASHINGTON STATE UNIVERSITY, Pullman, WA (US)

(72) Inventors: Georgina T. F. Lynch, Spokane, WA (US); Lars Erik Neuenschwander, Pullman, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 275 days.

(21) Appl. No.: 16/856,364

(22) Filed: Apr. 23, 2020

(65) Prior Publication Data
US 2020/0388400 A1 Dec. 10, 2020

Related U.S. Application Data

(60) Provisional application No. 62/837,498, filed on Apr. 23, 2019.

(51) Int. Cl.
*G16H 50/30* (2018.01)
*G09B 19/00* (2006.01)
(Continued)

(52) U.S. Cl.
CPC ............ *G16H 50/30* (2018.01); *A61B 3/0033* (2013.01); *A61B 3/112* (2013.01); *A61B 5/163* (2017.08);
(Continued)

(58) Field of Classification Search
CPC ........ G16H 50/30; G16H 10/60; G16H 40/40; G16H 40/63; G16H 50/20; G16H 50/70;
(Continued)

(56) References Cited

U.S. PATENT DOCUMENTS

| 2012/0268715 A1* | 10/2012 | Stark | A61B 5/163 |
| | | | 351/205 |
| 2013/0250244 A1* | 9/2013 | Yao | A61B 3/112 |
| | | | 351/221 |

(Continued)

OTHER PUBLICATIONS

Lynch et al. (Lynch, G. T. F., James, S. M., VanDam, M. (2017). Pupillary response and phenotype in ASD: Latency to constriction discriminates ASD from typically developing adolescents. Autism Research, 11(2), 364-375. https://doi.org/10.1002/aur.1888) (Year: 2017).*

*Primary Examiner* — Peter H Choi
*Assistant Examiner* — Chad A Newton
(74) *Attorney, Agent, or Firm* — WCF IP

(57) ABSTRACT

Neurological abnormalities are often discovered through observation by health care providers, and/or parent report. Many neurodevelopmental disorders such as ASD are purely identified through behavioral analysis, and cannot be screened for using a biomarker or quantitative stimulus-response test. Current screening tools contain subjective components based on parent report and clinician observation, vary in consistency of use across providers, and demands resources, knowledge, and access to skilled expertise. As a result, the only tests used today require lengthy and subjective behavioral analysis and often, miss or misidentify neurodevelopmental disorders contributing to a delayed diagnosis. The technology disclosed herein allow for a solution to this systemic problem.

3 Claims, 7 Drawing Sheets

(51) Int. Cl.

| | | |
|---|---|---|
| *A61B 3/00* | (2006.01) | |
| *A61B 5/00* | (2006.01) | |
| *A61B 5/16* | (2006.01) | |
| *G16H 70/20* | (2018.01) | |
| *G16H 50/70* | (2018.01) | |
| *G16H 10/60* | (2018.01) | |
| *G16H 70/60* | (2018.01) | |
| *G16H 50/20* | (2018.01) | |
| *G16H 40/40* | (2018.01) | |
| *G16H 40/63* | (2018.01) | |
| *A61B 3/11* | (2006.01) | |

(52) U.S. Cl.
CPC ............ *A61B 5/168* (2013.01); *A61B 5/4064* (2013.01); *A61B 5/4082* (2013.01); *A61B 5/4094* (2013.01); *A61B 5/7275* (2013.01); *G09B 19/00* (2013.01); *G16H 10/60* (2018.01); *G16H 40/40* (2018.01); *G16H 40/63* (2018.01); *G16H 50/20* (2018.01); *G16H 50/70* (2018.01); *G16H 70/20* (2018.01); *G16H 70/60* (2018.01)

(58) Field of Classification Search
CPC ........ G16H 70/20; G16H 70/60; G16H 20/70; G16H 15/00; A61B 3/0033; A61B 3/112; A61B 5/163; A61B 5/168; A61B 5/4064; A61B 5/4082; A61B 5/4094; A61B 5/7275; A61B 5/0059; A61B 5/4076; G09B 19/00
See application file for complete search history.

(56) References Cited

U.S. PATENT DOCUMENTS

| | | | |
|---|---|---|---|
| 2014/0104574 A1* | 4/2014 | Grenon ................ | A61B 3/1005 351/246 |
| 2016/0103338 A1* | 4/2016 | Hart ....................... | G02C 11/10 351/206 |
| 2016/0262613 A1* | 9/2016 | Klin ....................... | G16H 15/00 |
| 2016/0299354 A1* | 10/2016 | Shtukater ................. | G02C 7/04 |
| 2017/0311799 A1* | 11/2017 | Holt ........................ | A61B 3/152 |

* cited by examiner

\* indicates patient involvement

" " indicates a statement said by the provider to the patient

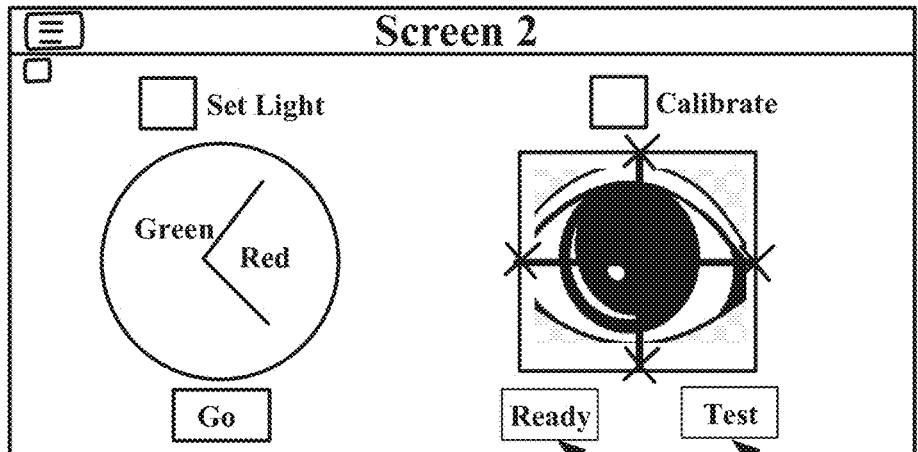
FIG. 8
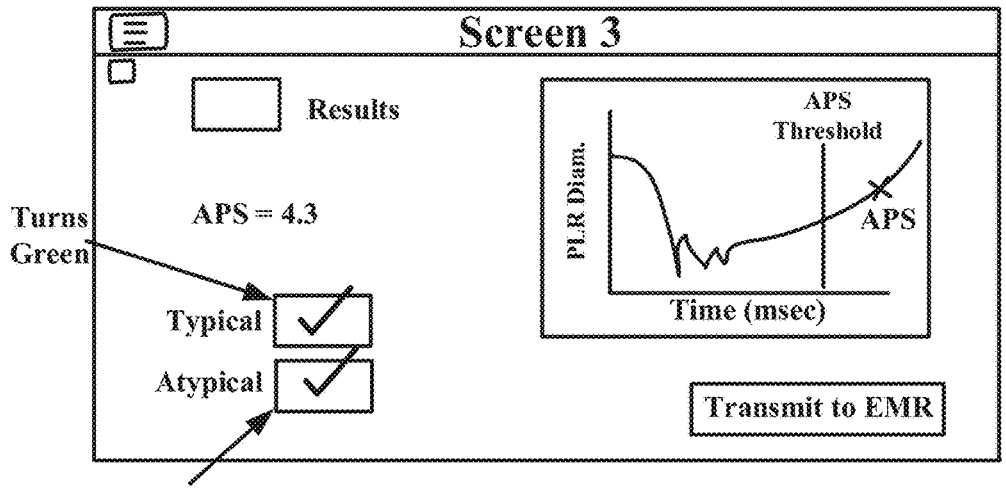
FIG. 9
FIG. 10

METHOD AND SOFTWARE FOR ASSESSING NEURODEVELOPMENTAL ABNORMALITIES

CROSS-REFERENCE TO RELATED APPLICATION(S)

The present application claims under 35 U.S.C. § 111(b), the priority benefit of U.S. Provisional Application No. 62/837,498 filed Apr. 23, 2019. The disclosure of the foregoing application is incorporated herein by reference in its entirety.

FIELD OF THE INVENTION

This invention generally relates to the field of biometric screening application systems, in particular, pupillary measurement and analysis for the diagnosis of neurodevelopmental abnormalities.

BACKGROUND OF THE INVENTION

Discussion of the Related Art

Pupillary measurement has served as a vital tool in the medical evaluation toolkit for the last 50 years. It is commonplace to test the pupillary light reflex (PLR), in which a light is used to stimulate the contraction of the pupil through a neurological system beginning in the retina moving to cranial nerves II & III and back to the sphincter and dilator pupillae muscles. It is a most helpful assessment for assessing neurological function specifically in response to Traumatic Brain Injury (TBI) such as concussion, stroke, brain death and more recently has implications in neurodevelopmental disorders such as Autism spectrum disorder (ASD), Attention deficit-hyperactivity/disorder (ADD), Down syndrome and more.

In the past when clinicians desired to evaluate the pupil they were required to do so using personal measurement techniques such as shining a pen light at the eye and looking for a response. This however lacked the specificity of quantitative output that can allow for distinct and exact risk assessments. More recently devices have been developed that allow for the quantitative pupil detection however these devices lack viable storage solution and algorithmic analysis capabilities.

SUMMARY OF THE EMBODIMENTS

In one embodiment disclosed herein it provides a computer-implemented method for initiating data collection, and outputting risk assessments for neurodevelopmental disorders or traumatic brain injuries utilizing the pupillary light reflex (PLR).

In another example embodiment of the disclosed invention, the method of interaction with an external hardware device, in the transitory storage medium comprises a centralized server and a plurality of outputs including software and hardware devices or cloud storage systems and the like. Further in the same embodiment of the invention the processor pulls from the device storage system into the internet in a secure cloud system and out of the cloud.

Further in another example embodiment, the device can be utilized in the capture of actions required to analysis the pupillary light reflex. Including the auto-generation of progress reports, and training protocols.

In another example embodiment the user interface system for the calibration, interaction and use of a combinatorial device is modified to be acceptable to any age. Additionally, such an example embodiment describes the system through which patient data is anonymized and retrieved by the application user.

In another embodiment is a user interface system for the pairing of an external device through a secure network connection with key connections described.

In another embodiment herein is a method for assessing autism comprising a data collection period to include collecting a data set from one or more data collection devices; and determining, via the data set and by the light levels, based at least in part by the pupillary change in measurement of the subject, a risk assessment of autism spectrum disorder in the subject.

In another embodiment herein is a method for acquiring patient data with patient compliance and innovative features of patient provider interaction prompting including order or phrasing. In another embodiment herein is a method for recording and assessing whether the pupil recording meets the criteria for recording and evaluation.

Another embodiment herein is a method for assessing neurodevelopment disorders comprising: initiating data collection with an established protocol and a data collection device followed by collecting the data from one or more data collection devices. Once data collection is complete, the data related to light levels in at least one part by the pupillary change in measurement of the subject will be used to produce a risk assessment of a neurodevelopment disorders in the subject. Once an assessment is complete, it is transmitted to a recording system, medical record or the like.

Another embodiment herein is a method to control a data collection device comprising: calibrating of a data collection device and capturing data baseline data with the data collection device. After which, baseline data is transferred to a recording system, wherein data capture for the data collection device is initiated from the subject. Finally, the captured data is analyzed to assess risk of a neurodevelopment disorder in the subject.

In yet another example embodiment of the invention, the symptoms resulting from a neurodevelopmental disorder further include the assessment of co-morbidities associated with the neurodevelopmental disorder. Such comorbid conditions include, but are not limited to, seizure disorder, epilepsy, sleep disorders, metabolic disturbance, gastrointestinal disturbance, autoimmune disorder and/or allergies, restrictive repetitive behaviors including, but not limited to, forms of obsessive compulsive disorder, depression, eating disorders, anxiety disorders, and the like. Documented basic physical parameters will be included in the assessment capability, including but not limited to, height, weight, head circumference, in relation to available comparative growth curves by age and sex.

The foregoing and other objects, features, and benefits of the present disclosure will become more apparent from the following detailed description, which proceeds with reference to the accompanying figures.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8 shows an example Graphical User Interface (GUI) Screen procedure.

FIG. 9 shows another example Graphical User Interface (GUI) Screen procedure.

FIG. 10 shows another example Graphical User Interface (GUI) Screen procedure.

DETAILED DESCRIPTION

Figure 1:
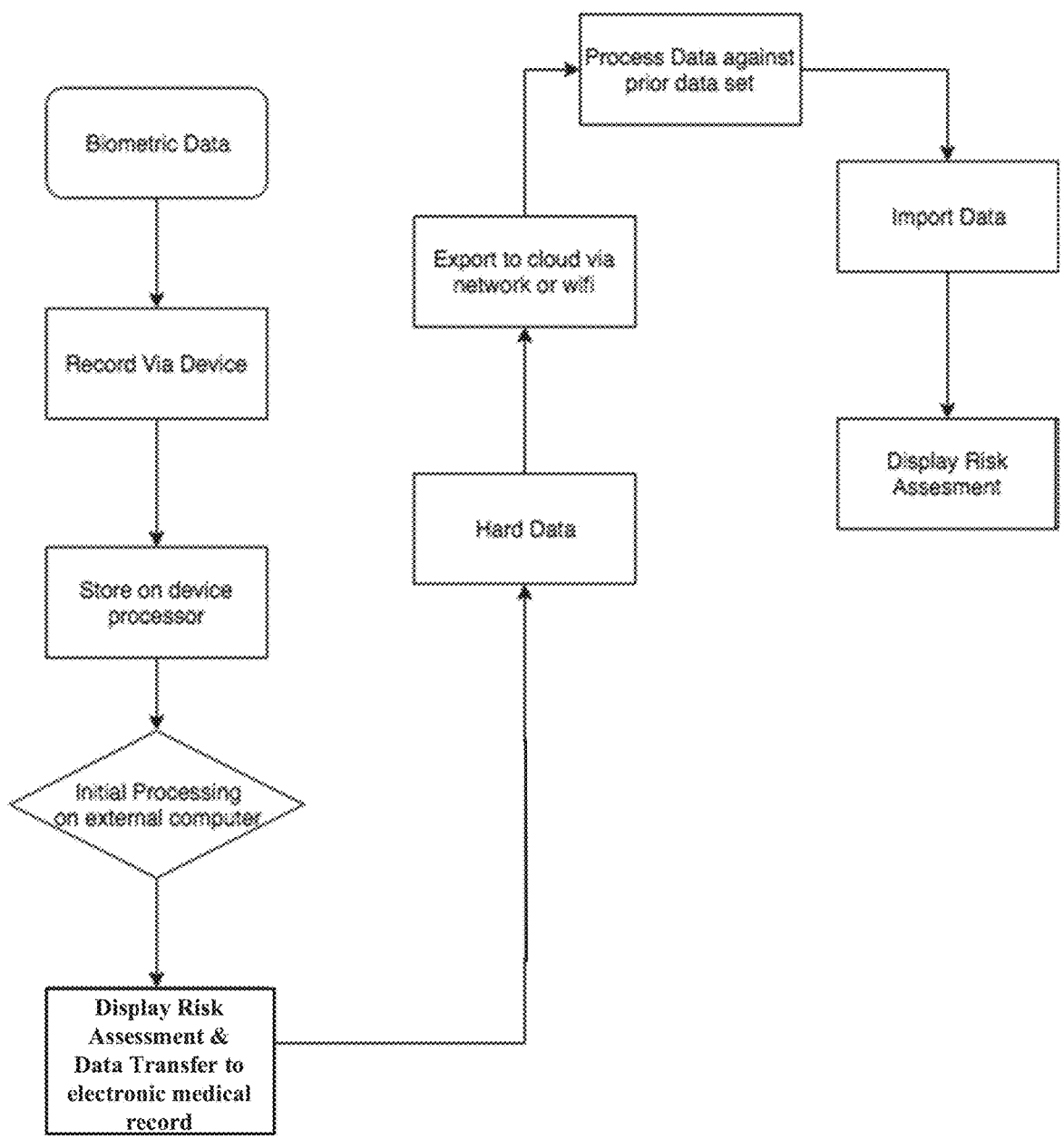
FIG. 1 shows an example method through which biometric information is taken from an external device and loaded into an electronic medical record and optionally, loaded into the cloud for future information display.

The following are definitions of terms that may be used in the present specification. The initial definition provided for a group or term herein applies to that group or term throughout the present specification individually or as part of another group, unless otherwise indicated.

Additionally, it will be understood that any list of such candidates or alternatives is merely illustrative, not limiting, unless implicitly or explicitly understood or stated otherwise.

As used in this specification and the appended claims, the singular forms "a", "an" and "the" include plural referents unless the content clearly dictates otherwise.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the term "condition" or "disorder" refers to a symptom that a subject represents, such as, but not limited to, anxiety, Obsessive-compulsive disorder, attention deficit-hyperactivity disorder, schizophrenia, autism or ASD.

The use of the term "treating," "treatment," or "therapy" of a disease or disorder means slowing, stopping, or reversing progression of the disease or disorder, as evidenced by a reduction or elimination of either clinical or diagnostic symptoms, using the compositions and methods of the present invention as described herein.

The use of the term "data collection device" refers to an instrument that allows for comparison means, such as a computer processor, for comparing data received from the optical element of the device. The data collection device further comprises communication means for providing communication to the end user in the event that data received by the detection means and the optical character assess a problem. The communication means may comprise a wire. Alternatively, the communication means may comprise a wireless communication means for transmitting data via a wireless network, or a secure wireless network.

The data collection device may also comprise a data storage system, such as a hard disk drive or flash memory device. In some embodiments the data collection device is adapted to be capable for communicating with a medical device. In another alternative embodiment, the data collection device is further configured to be capable of arranging and modifying data within the data set, wherein the data is configured to be in communication with the end user.

In another alternative embodiment, the data collection device may further comprise a user interface that is capable of communicating with a storage system so as to enable the end user to selectively access, modify, and/or supplement the data within the data set.

In addition, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

Autism spectrum disorder is a neurodevelopmental disorder whose diagnostic criteria are a persistent disorder in social communication and interrelationship, and a limited and repetitive manner of behavior, interest, and activity. Conventionally, autism (disorder) has been classified as a type of pervasive generalized developmental disorder. However, according to the *Diagnostic and Statistical Manual of Mental Disorders, 5th Edition* (DSM-5), which is used to diagnose autism spectrum disorder, these four sub-diagnostic items for pervasive developmental disorder (autistic disorder, childhood disintegrative disorder, Asperger's Syndrome, pervasive developmental disorder, not otherwise specified-PDD-NOS) are no longer specified under the diagnostic term autism spectrum disorder for the provision of healthcare. The diagnostic term is autism spectrum disorder and represents a continuum of deficits described above.

Detection of abnormalities in the brain response is possible using the PLR in a quantitative assessment, through evaluating measurements comprising latency to constriction, constriction time, or base pupil diameter or return to baseline diameter or max constriction diameter or a combination of all of these measurements.

It is desirable to be able to detect any of the injuries or disorders spoken about in the above section early in their progression. The young may face more difficult living circumstances due to a delay in diagnosis for neurodevelopmental disorders. This may have vast implications for quality of life for these children. Moreover, pupillary detection can have preventative or predictive implications, helping to predict outcomes during the developmental period and post TBI and informs clinical procedures.

A developing research line measuring the pupillary light reflex (PLR) in children with autism spectrum disorder (ASD) and typically developing children has provided a basis for disclosing a mechanism by which health care providers could be trained to assess the PLR using software technology which can either assist in the collection of the measurements, or guide the procedures for obtaining and interpreting the PLR measure as typical or atypical. Additionally, storing the data for transmission via electronic portal to share information between health care providers for ongoing monitoring of maturation of the visual pathway over time early in development when measured at each routine developmental health exam conducted by a health care provider or pediatrician. The PLR metric may be used to support earlier detection of ASD, and has the potential to change healthcare practices in relation to screening of ASD by over 75,000 currently practicing pediatricians in the United States. The pediatrician is currently the primary health care provider making initial decisions in the screening process and working with the family to seek out comprehensive diagnostics. Multiple health care providers are involved in gathering physical measurements of children to inform diagnostic decisions, including the use of non-diagnostic screening tools. Providers need an objective biomarker to support that process so children will have access to intervention earlier.

An additional factor to consider is that pupillary measurement can be subjective and not all patients may require or receive the same response from clinicians. More specifically for some situations, which an individual would consider an emergency, the clinician may wish to evaluate the pupil for state of life where as in other situations they may want to evaluate the pupil amongst other key metrics for further resulting diagnostic capabilities.

In today's diagnostic workup for autism spectrum disorder, a questionnaire examining social communication and behavior is used to evaluate the well-being and development of the child at 18 and 24 months of age to determine potential atypical behavioral characteristics in relation to development. This questionnaire, the *Modified Checklist for Autism in Toddlers, Revised with Follow-Up* (M-CHAT-R/F©) has varying sensitivity and specificity depending on the child's medical history, age, and subjective responses from the parent/caregiver. The M-CHAT-R/F© yields a cut-off threshold for risk associated with ASD and is used by the physician to determine whether or not to move forward with a comprehensive diagnostic evaluation, which in current practice typically includes administration of the *Autism Diagnostic Observation Schedule, Second Edition* (ADOS™-2) which is performed in the clinic with the diagnosis being performed by the pediatrician or clinical psychologist in most cases. Today's prevalence rates indicate the average age of diagnosis for a child with ASD is 48 months old. Following an ASD diagnosis parents are advised to enroll their children in therapy programs to assist and monitor development. These programs are much more impactful the younger the child is, with the most optimal window of time for treatment to be effective, occurring between the ages of 24 months and 60 months.

Current questionnaires provide a limited scope of autism assessments relying on behavioral methods. Questions on the M-CHAT-R/F can be useful in the toolkit of the developmental pediatrician to inform the progress of neurodevelopment in children, however they are not used to give a defined risk assessment and lack both biometric and time progression capabilities.

Specific Description

In an example embodiment of the disclosed invention it can be operated on a encased hand-held device with connection capabilities to a local security protected computer network, and may be uploaded to a cloud server global computer network Wherein a plurality of computer systems around the world are in communication with one another via this global computer network.

In another embodiment of the disclosed technology, the data collection device can be affixed to a wall or other stationary surface, as detailed below. Additionally, the data collection device can be attached or removably coupled to an extension apparatus allowing for movement in all directions while affixed to the wall or other stationary surface. During the assessment the end-user navigates a series of readings, questionnaire's, device trainings, and simulations.

Training and monitoring may serve as a method of containing device operations. The PLR can be captured once lighting and calibration with the pupil are in sync with valid PLR conditions, which is conveyed to the end user.

An example methodology of the disclosed invention can be seen in FIG. 1, wherein an external device (e.g., see FIGS. 7A and 7B and corresponding discussion below) capable of recording biometric data, including but not limited to, the pupillary light reflex together with the embedded micro-processor and an operating system operate to transfer store, process and upload data into a secure cloud and other of the like. The device will have the ability to capture data and provide an output in real time. Optionally collected data and outputs can be saved to a secure cloud for later retrieval or review.

In an additional embodiment the data can be collected and processed before any data is transferred, where-in further processing occurs and hard data points are uploaded and to the internet and processed further to inform a risk assessment for injury or neurodevelopmental delays.

Computer code may reside at any point in this process, on the device (e.g., firmware), or RAM or storage, or in the internet. In an exemplary method, a network interface circuit is used to upload the data to the internet as well as off the internet utilizing code on the device.

Figure 2:
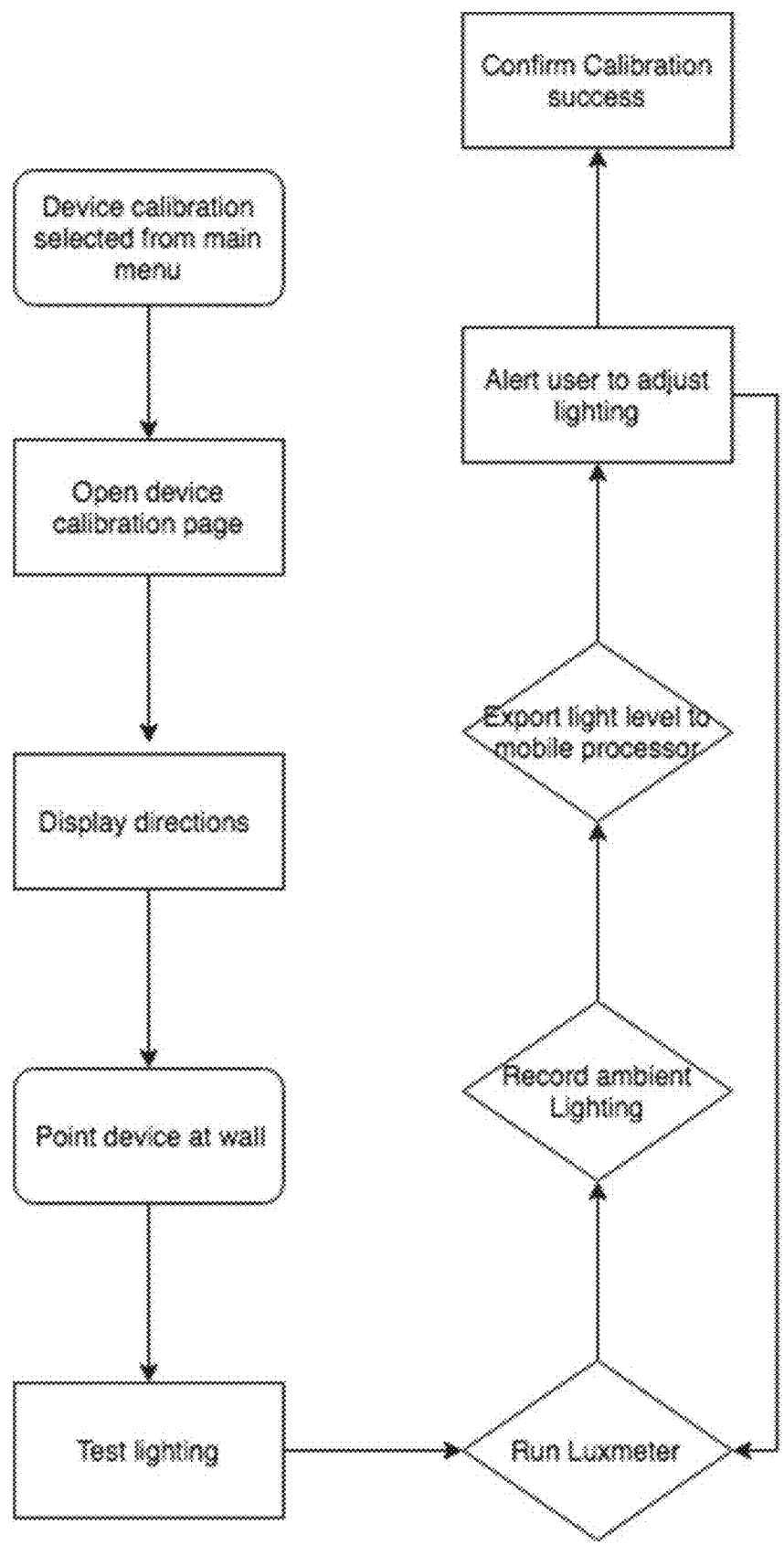
FIG. 2 show another example process through which an application user can calibrate an external device based off of key parameters including, directionality, pairing, light calibration, and pupillary dilation.

Device calibration will occur in a step-wise manner. The first step comprises opening a landing page on the device. The second step involves pointing the image capturing device at a blank surface and pressing calibration on the landing page. The second step utilizes a series of algorithmic operations including but not limited to, utilizing a microprocessor, external computer, and circuit board to turn on an external digital light sensor, record lighting conditions, process and store this information in RAM or other storage source, and export this information to where the end-user will be informed how to manually adjust the ambient lighting to be effective. This value will be determined by an existing code residing on the device. The third step will output to an end user a confirm of adequate lighting conditions. Such processing steps are depicted in FIG. 2.

Additional metrics for the device calibration were developed to provide combining the latency to constriction pupillary parameter with a return to baseline (RTB) pupillary parameter. The RTB is often defined as pupil diameter returning to 75% of baseline after elicitation of constriction based on a 5,000 ms recording time and allows for the discrimination of the typical development when compared to children without autism from a child with autism spectrum disorder (ASD). Thus, the metric serves as a biometric screener for typical vs. atypical PLR and potential atypical maturation of the visual neural pathway, deemed "at risk" for neurodevelopmental delay when greater than or equal to 3,000 ms latency and ≤75% RTB.

The age of the subject and a subject specific identification number are also entered into the device for analysis of PLR in relation to chronological age and sex. In one embodiment, the examination can be done in lighting conditions that are dimmed or ambient conditions, such as a lighting condition from 1 lux up to 20 lux.

The user interface (e.g., a graphical user interface (GUI)) between a sensor and microprocessor in a device which processes lighting conditions codes the condition through software to indicate environmental condition accuracy using a simple visual signal to the user. The visual signal indicates target PLR conditions for taking the measure. Once conditions are met, the software indicates an acceptable zone for taking the measurement. A behavioral and verbal protocol can also be used to guide the subject to look toward the light. The recording is taken 2 trials per eye, right eye, left eye, right eye, left eye, in that sequence. Each trial is shown as complete on the display as the provider takes the measure. The software indicates success or failure to capture the recording after each elicitation. The recording of the eye is shown to the patient by the provider.

The software codes the PLR metric defined above and generates the latency to constriction+RTB metric and aligns this with chronological age for latency to constriction (in milliseconds), RTB (in percentage/decimal from 0-1), and a combined total metric (in percentage 0-1). The combined metric is scaled against the two measures above to yield a "positive pupillary response" (PPR) vs. "negative pupillary response" (NPR) and identified in a numeral code with the letter code PPV and a separate numerals code to indicate a negative response with the NPR letter code. The RTB metric and constriction time measures are further assessed in relation to a time threshold in milliseconds, to differentiate the Autism Pupil Score, or "APS", based on a delayed response of the pupil.

Figure 3:
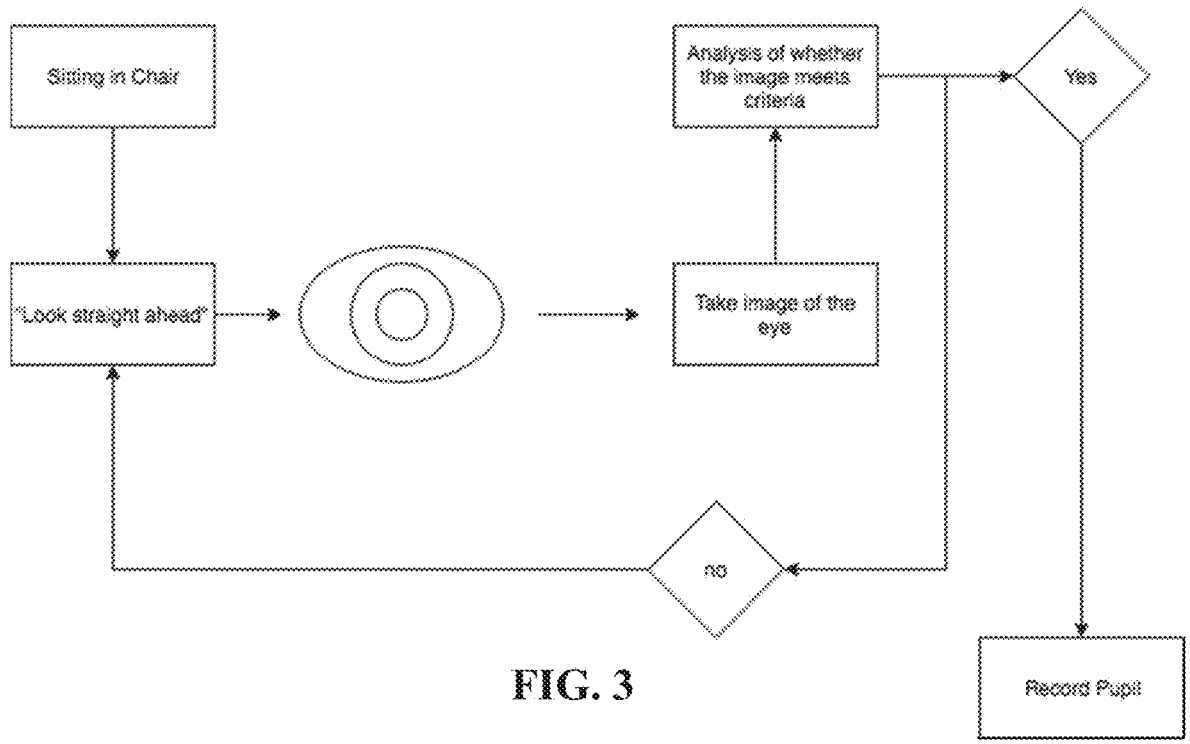
FIG. 3 shows an example method for data capture that occurs in a clinical setting.

FIG. 3 graphically depicts a method wherein providers are instructed in pupillary data acquisition. As detailed FIG. 3 shows a step wise system through which pupillary data is identified by either software or user and identified as meeting criteria important to data importation. These may include but are not limited to: position of the pupil in the image, alignment correct distance from the capture apparatus or timing.

Figure 4:
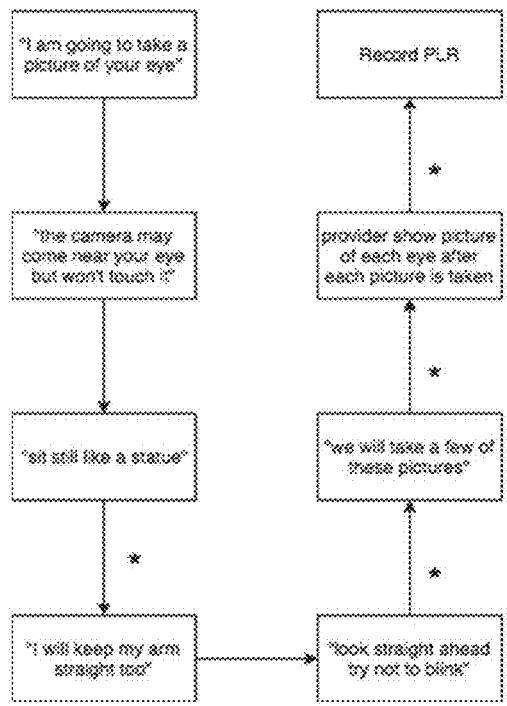
FIG. 4 shows an example method through which a patient and tool user interact in order to best obtain patient compliance through the data acquisition process.

FIG. 4 illustrates a method for intaking the patient using behavioral cues. The patient must be prompted in a set order, including statements such as "sit still like a statue" for one non-limiting example, which have been tested in scientific setting and identified as an innovation in the method for patient data acquisition and patient cooperation in the data acquisition process. A visual schedule depicting images describing each step of the test administration process is paired with these statements, tested in a scientific setting and shown to reliably assist in data acquisition of the PLR in the ASD population.

Once data is collected, the PLR metrics are coded to a number, date of recording, age at time of recording, and coded to a visual graph indicating performance in relation to typical development by age. The software will have two capabilities: sync to a local medical record system and the option to send to an ePHI protected server for transmission to another provider or medical record system.

Figure 5:
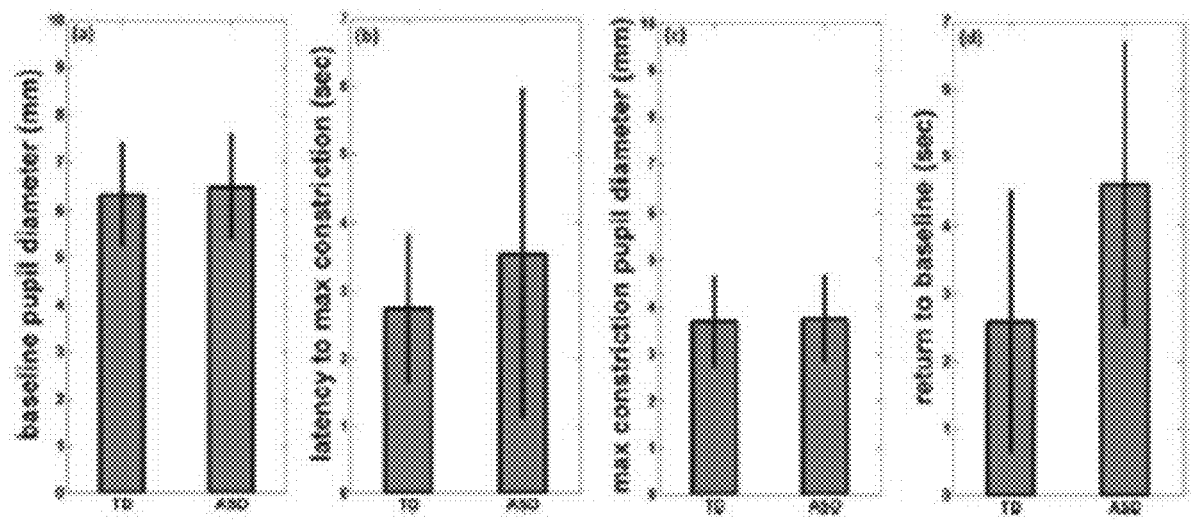
FIG. 5 shows the mean pupillary measures of diameter and latency for autism spectrum disorder (ADS) and typically developing controls (TD) groups at a) baseline, b) Latency to maximal constriction, c) maximal constriction, and d) RTB latency.

FIG. 5 shows the mean pupillary measures of diameter and latency for ADS and TD groups at a) baseline, b) Latency to maximal constriction, c) maximal constriction, and d) RTB latency. To further evaluate the collected data and relate it to a diagnosis. The PLR is used to establish an Autism PLR Screening (APS) score that represents constriction latency and RTB pupil parameter thresholds of the PLR using the data collected from the device. The data shows a 72% sensitivity for diagnosis ASD using the combined RTB and latency to contraction parameters when compared to typical methods. Additionally, it identified a threshold of greater than 3,000 milliseconds in ASD, considered a sluggish pupillary light reflex clinically in comparison to typical development, demonstrating an average of 2,000 millisecond latency. The RTB metric provides a measure of the visual neural pathway responding in relation to homeostasis, and when combined with latency to constriction, serves as the APS score.

Figure 6:
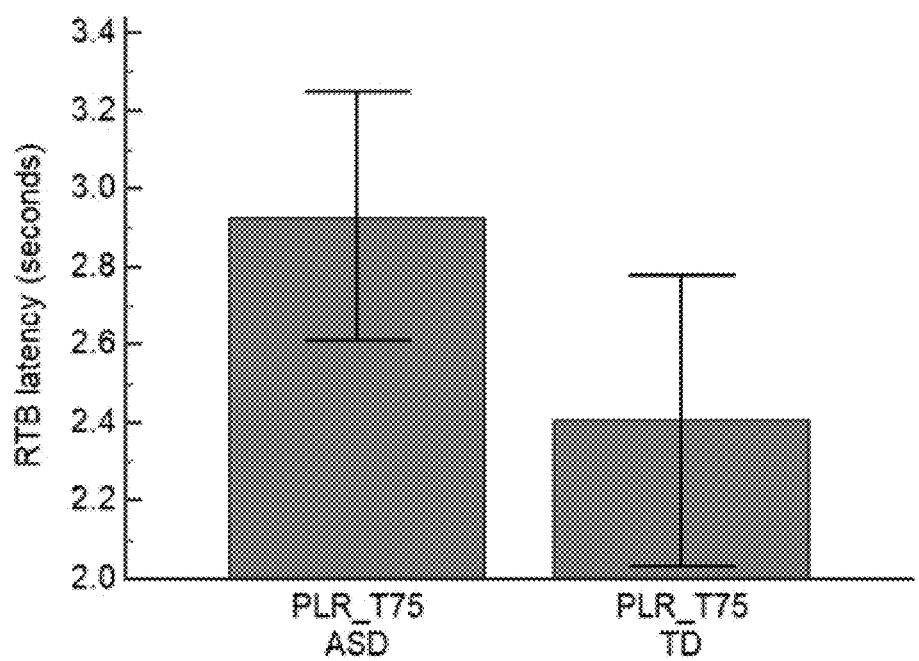
FIG. 6 shows independent samples t-test for $C_{t1}$ indicated relatively slower constriction time for the TD group (ASD M=0.69; TD M=0.80; t(208)=2.907; p<0.05). Comparison of RTB T75 between groups revealed significantly greater latency for rediation to 75% of baseline pupil diameter in the ASD group (ASD, M=2.94; TD, M=2.37; t(209)=−2.264; p<0.05.).

Thus, the APS score is used to interpret typical from atypical PLR response based on a threshold of ≥3.78 ms. In 45% of ASD cases, the PLR did not return to baseline, demonstrating significantly greater latency than the APS threshold, exceeding the standard 5,000 ms recording duration, as can be seen in FIG. 6.

The APS score is then also utilized as a metric for data processing in the software. As utilized in the software, the APS score is calculated according to an RTB metric set at the time interval in which the pupil returns to 75% of baseline pupil diameter and yields an interpretation threshold for typical vs. atypical development based on positive predictive values (PPV) and negative predictive values (NPV) for the presence of the disease/disorder, in this case identifying ASD. Receiver operating characteristic (ROC) analysis was conducted to identify ROC curves using a criterion threshold based on the RTB parameter to determine signal detection based on latency of return to 75% of baseline pupil diameter after presentation of the light stimulus. This variable was used to determine discriminant ability of the model for identifying ASD compared to TD using a disease prevalence of 1.46%.

The PLR parameters of baseline pupil diameter and maximum constriction pupil diameter revealed no difference between groups. PLR data analysis for each PLR parameter using logistic regression to evaluate predictive ability of the PLR parameters are also used to identify the categorical variable of ASD diagnostic status. PLR measurements are processed and analyzed based on these PLR parameters. Results of the regression model examining indicated significance for each of these parameters as a positive predictor of ASD.

The ROC analysis identifying thresholds for a positive APS score reveal a specificity criterion of ≥3.5 seconds for RTB. As shown below in Table 1 below, the confidence intervals, specificity, and PPV rates for ASD based on the analysis of the PLR RTB metric.

TABLE 1

| Criterion | Sensitivity | 95% CI | Specificity | 95% CI | +LR | −LR | +PV | −PV |
|---|---|---|---|---|---|---|---|---|
| >2.21 | 50.00 | 41.6-58.4 | 59.57 | 49.0-69.6 | 1.24 | 0.84 | 1.8 | 98.8 |
| >2.24 | 49.31 | 40.9-57.8 | 59.57 | 49.0-69.6 | 1.22 | 0.85 | 1.8 | 98.8 |
| >2.34 | 49.31 | 40.9-57.8 | 60.64 | 50.0-70.6 | 1.25 | 0.84 | 1.8 | 98.8 |
| >2.37 | 49.31 | 40.9-57.8 | 61.70 | 51.1-71.5 | 1.29 | 0.82 | 1.9 | 98.8 |
| >2.47 | 49.31 | 40.9-57.8 | 62.77 | 52.2-72.5 | 1.32 | 0.81 | 1.9 | 98.8 |
| >2.54 | 48.61 | 40.2 -57.1 | 62.77 | 52.2-72.5 | 1.31 | 0.82 | 1.9 | 98.8 |
| >2.71 | 47.92 | 39.5-56.4 | 63.83 | 53.3-73.5 | 1.32 | 0.82 | 1.9 | 98.8 |
| >2.81 | 47.22 | 38.9-55.7 | 63.83 | 53.3-73.5 | 1.31 | 0.83 | 1.9 | 98.8 |
| >2.84 | 46.53 | 38.2-55.0 | 64.89 | 54.4-74.5 | 1.33 | 0.82 | 1.9 | 98,8 |
| >3.04 | 46.53 | 38.2-55.0 | 67.02 | 56.6-76.4 | 1.41 | 0.80 | 2.0 | 98.8 |
| >3.18 | 45.83 | 37.5-54.3 | 69.15 | 58.8-78.3 | 1.49 | 0.78 | 2.2 | 98.9 |
| >3.24 | 45.83 | 37.5-54.3 | 70.21 | 59.9-79.2 | 1.54 | 0.77 | 2.2 | 95.9 |
| >3.54 | 45.14 | 36.8-53.6 | 70.21 | 59.9-79.2 | 1.52 | 0.78 | 2.2 | 98.9 |
| >3.61 | 44.44 | 36.2-52.9 | 70.21 | 59.9-79.2 | 1.49 | 0.79 | 2.2 | 98.8 |
| >3.74 | 44.44 | 36.2-52.9 | 71.28 | 61.0-80.1 | 1.55 | 0.78 | 2.2 | 98.9 |
| >3.78 | 44.44 | 36.2-52.9 | 72.34 | 62.2-81.1 | 1.61 | 0.77 | 2.3 | 98.9 |
| >5 | 0.00 | 0.0-2.5 | 100.00 | 96.2-100.0 |  | 1.00 |  | 98.5 |

The APS score is calculated based on the PLR and given user-interface interpretation output for documenting, transferring, and storing the recorded data and providing a real time read out of the date or transferring the date to a medical record or other of the like.

Pupillometer System, Display, Wall Mounting Support Mechanism

Figure 7:
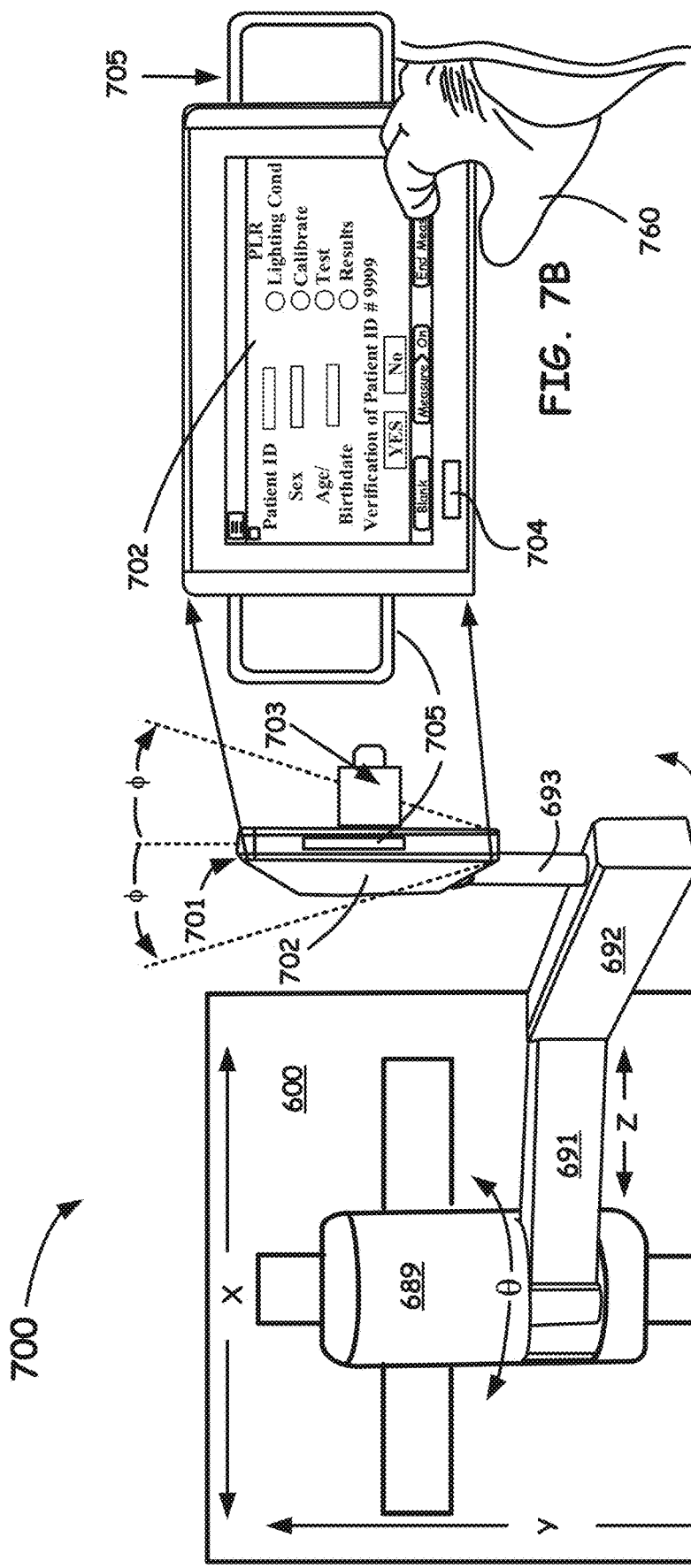
FIG. 7A shows an example wall-mounted pupillary analysis system, as disclosed herein.
FIG. 7B particularly illustrates the Graphical User Interface screen of the wall-mounted pupillary analysis system, as disclosed herein.

To further appreciate the embodiments described herein, the invention also provides an optical interrogation apparatus (e.g., a pupilometer, as generally referenced by the numeral 700), display, and data collection system, as shown in FIG. 7A and FIG. 7B that is not necessarily drawn to scale. Such a pupillometer system 700 enables monitoring and comparing in real-time the response of an individual's left and right pupils to a stimulus, such as a light stimulus, auditory stimulus, or noxious stimulus. In particular, the pupilometer 700 system disclosed herein is configured to stimulate an eye response with configured light pulses and thereafter collect and analyzes the resultant captured sequence of images (often digital images) to result in desired temporal measurement(s) of the diameter of an individual's pupil. The intensity and duration of the light stimulus can be set by the user of pupillometer 700 using easily found GUI controls on display 702. The images themselves result from a lensing system, illumination source (e.g., an infrared illumination source), and a camera all shown generally by the reference numeral 703. Image information, using embedded software, is provided to a user via the screen 702 that also operates as a Graphical user interface (GUI).

Turning back to the discussion for FIG. 7A and FIG. 7B in particular, the system shown as a wall mounted pupillometer 700, generally includes a graphical user Interface (GUI) display 702 for touch screen capabilities by a user 760 (hand shown for simplicity), a coupled lensing system 703 for pupil imaging measurements, one or more handles 705 for maneuvering the pupillometer 700, one or more input/output ports 704 (one shown for simplicity), a wall 600 mounting component 689 that enables an angular movement coupled to a plurality of maneuverable mounts 691, 692, and 693 (e.g., having a hinge mechanism) that enables degrees of movement q, α, and f respectively. Moreover, wall 600 mounting component 689 can ride in X and Y directions based on existing technologies and maneuverable mounts 691 can provide Z direction movement for coupled mount 692 all of which in combination with the angular capabilities provides every degree of movement necessary for ease of alignment.

It is also to be noted that the display screen 702 (e.g., an iPAD) aspect that utilizes a Graphical User Interface (GUI)), enables not requiring a keyboard, an additional processor, or even an additional larger display screen. Moreover, the screen (GUI) of which includes virtual selective choices allows the instrument(s) herein to remain small enough and lightweight enough so as to be easily and conveniently be decoupled from the mounting mechanism so as to also have the capability of being utilized as a hand-held device depending on the needs of the user or moved to another location if desired for perhaps mounting elsewhere.

It is also to be appreciated that the instrument herein is often preferably configured as a standalone unit, wherein the display is configured with a high-resolution, touchscreen interface and as a tablet-based operating system with features for guided method analysis provided to save an operator time and bench space. In addition, auto-measure features configured with embedded software adds speed and convenience delivering results with full data sets rapidly. The instrument(s) herein also are configured to enable outputting data (e.g., I/O port 704 using configured USB and/or Ethernet configurations, Wi-Fi or an external computer that can also direct information to the cloud. Such capabilities enable flexibility for extended analysis and electronic archiving.

Moreover, while a Liquid Crystal Display (i.e., an LCD display) preferably a flat panel display, is often mentioned herein as the display 702, it is to further be appreciated that other display devices, such as, but not limited to, electroluminescent displays, Organic light-emitting diodes (OLED) displays, Field emission displays (FEDs), Single emission displays (SEDs), or other known flat panel displays can be utilized by the embodiments herein where desired and where such devices do not depart from the spirit and scope of the present application.

While not shown detailed, the I/O portion 704 enables various means of communication using known methods to those skilled in the art. For example, in some embodiments, instrument 700 can be connected to other devices via the I/O portion interface over other types of networks, including isolated local area networks and/or cellular telephone networks. The connection can also be a wireless connection or a physical coupling. As non-limiting examples of a wireless connection, such an arrangement can include commercial wireless interfaces, such as but not limited to, radio waves (WiFi), infrared (IrDA), or microwave technologies.

The wireless network can, for example, be configured with Bluetooth, which operates in a globally available frequency band (i.e., 2.4 GHz), ensuring communication compatibility worldwide, or wireless network can be Electronic and Electrical Engineers IEEE technologies (e.g., (IEEE) 802.11a or IEEE 802.11b) as the communication means based on its present common use in both business and home environments. Such popular technologies enable users' high-speed access to networks and the Internet. Moreover, other protocols for wireless, such as IEEE 802.15, IEEE 802.16, GPS, 3G and others, may also be configured as a protocol for the communication standard of the present embodiments disclosed herein. Data can also be transferred seamlessly to a PC or Network via, for example a USB port or Wi-Fi for electronic archiving or printing. As another beneficial embodiment, an external keyboard or mouse can also be coupled to the instrument 700 via, for example, Bluetooth® if even greater flexibility is desired.

With respect to a physical wired coupling aspect, the coupling can be by way of a dedicated coupling I/O means, such as an Ethernet cable or the aforementioned USB port to provide, for example, operational data transfer via an embedded software (e.g., firmware) in instrument 700 or instructions received from, in some operations, a coupled processor or aforementioned wireless connectivity.

It is to be noted that the instrument 700 embodiments disclosed herein can further be configured with individual software modules, components, and routines in the form of a computer program, procedure, or process written as source code in C, C#, C++, Java, and/or other suitable programming languages. The computer programs, procedures, or processes may be compiled into intermediate, object or machine code and presented for execution. Various implementations of the source, intermediate, and/or object code and associated data may be stored in one or more computer readable storage media that include read-only memory, random-access memory, magnetic disk storage media, optical storage media, flash memory devices, and/or other suitable media.

A computer-readable medium, in accordance with aspects of the present invention, refers to media known and understood by those of ordinary skill in the art, which have encoded information provided in a form that can be read (i.e., scanned/sensed) by a machine/computer/processor and interpreted by the machine's/computer's/processor's hardware and/or software. It is also to be appreciated that as used herein, the term "computer readable storage medium" excludes propagated signals, per se.

Turning back to the discussion for the Graphical User interface, FIG. 8 shows an example GUI screen that enables configuration for developing pupil measurements of an individual. As an illustrative procedure, the GUI screen 702 can be prompted to display, for example, a first screen (e.g., deemed Screen Level 1), wherein prior to conducting a PLR assessment, input is requested for the, Patient ID #, Sex, Age coupled with birthdate, and, (e.g., M=1; F=0) and is entered into the hardware device using the GUI to provide data for analysis of PLR in relation to chronological age and comparative growth curves by age. The user/provider is asked to verify Patient ID #selecting, [GREEN] [YES] or [RED] [NO] as shown in FIG. 8 and then selects from a menu of four processes to complete: Lighting Condition, Calibrate the system 700. Note that each process opens to an appropriate screen.

FIG. 9 shows an example GUI screen that opens up deemed GUI Screen Level 2. This procedure occurs in dark adapted conditions (1 lux). The Lighting Condition option is selected and reads the ambient lighting for optimal PLR collection and reports back to the user via a sensor and microprocessor in a hardware device which processes lighting conditions then codes the condition through custom software to indicate environmental condition accuracy using a simple visual signal to the user. The visual signal indicates a "green zone" for taking the measurement. A circle rotating from [RED] as the environmental lighting adjusts, to [GREEN] with word "GO" to align the tool to the eye and begin calibration. A behavioral and verbal protocol displays to guide the child to look toward the light "taking a picture of the individuals eye". The recording is taken 2 trials per eye, right eye, left eye, right eye, left eye, in that sequence. The software indicates success or failure to capture the recording after each elicitation. The "picture"/recording of the eye is shown to the patient by the provider. The user selects "CALIBRATE" and the eye is located on the screen—when all five points are in alignment for calibration, the word "READY" will light up in [GREEN] and "TEST" will light up in [GREEN]. Select TEST R1 for first test of right eye, TEST L1 for first test of left eye, TEST R2, for second test of right, TEST L2 for second test of left eye. The "TEST" cell will light up [RED] as recording. Each trial is shown as complete on the hardware display as the provider takes the measure. When all 4 PLRs are captured, the screen reads TESTING COMPLETE across face of the screen. The menu of 4 original options reappears, and the user selects "RESULTS".

FIG. 10 shows an example GUI screen that screen that opens up deemed GUI Screen Level 3.GUI Screen 3: Here the user selects a cell indicating "RESULTS" to obtain the interpretation metric. The processor codes the PLR metric and generates the latency to constriction+RTB values to compare against typical PLR metrics by chronological age for latency to constriction (in milliseconds), RTB (in percentage/decimal from 0-1), and a combined total metric (scaled based on a time threshold). The combined metric is scaled against the two measures above to yield a "positive pupillary response" (PPR) vs. "negative pupillary response" (NPR) and identified by a visual indicator for "TYPICAL" [GREEN] with the letter code PPR and value, or "ATYPICAL" [RED] with the NPR letter code and value.

Results yield a real-time Autism Pupil Screening (APS) score indicating a threshold of PLR response plotted above or below, which contributes to the results of "TYPICAL" vs. "ATYPICAL" for the PLR based on age, sex, and comparative typical PLR data incorporated into the processor. A value based on the discriminant threshold for constriction time and RTB in relation to the comparative dataset is used to identify this score.

Figure 11:
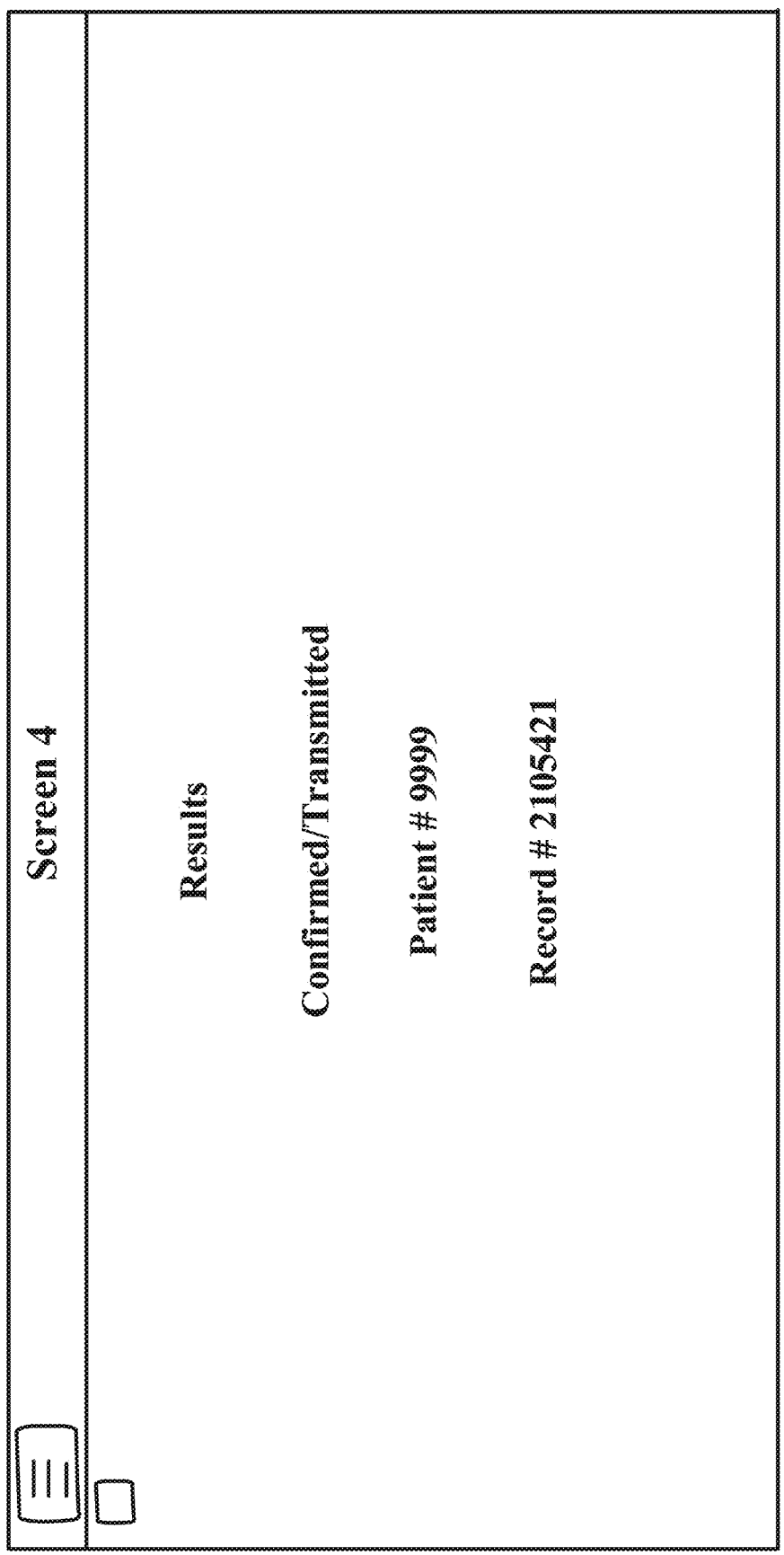
FIG. 11 shows yet another example Graphical User Interface (GUI) Screen procedure.

FIG. 11 deemed Screen level 4 shows where the user then chooses to transmit the score and interpretation to the electronic medical record by selecting the "Transmit to EMR" cell. Data can be viewed for each individual patient mapped onto a comparative growth curve for PLR for metrics tested by age to view results and/or explain results in the context of typical development.

It should be emphasized that the above-described embodiments and following specific examples of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

We claim:

1. A computer-based method for risk assessment, in early progression, of neurodevelopment disorders, comprising steps performed on a movable device that includes a computer coupled to a computer-readable storage medium, a hardware display, a digital light sensor, a computer controllable lensing system, a camera, and a pulsed illumination source, the steps comprising:
  A) on the hardware display opening a first level graphical user interface (GUI) screen, and displaying in the first level GUI screen an age-gender field and a plurality of processing menu cells, including a process menu first cell that provides for selecting of a lighting level process, and a process menu second cell that provides for selecting of a test results process;
  B) in response to receiving a subject's age and gender in the age-gender field, storing the age-gender in the computer-readable storage medium;
  C) in response to receiving the selecting, via the process menu first cell, of the lighting level process, opening on the hardware display from the first level GUI screen to a second level GUI screen, displaying in the second level GUI screen a light level indicator field, an alignment indicator field, an alignment process selection cell that provides for selecting an eye alignment process, and a measurement process selection cell that provides for selecting a pupillary light reflex (PLR) measuring process, and
    1) reading the digital light sensor and based on said reading displaying in the light level indicator field an ambient light indicator, having visible reference to an acceptance zone, and
    2) repeating (C)(1) until detecting the measured ambient light level being within the acceptance zone, and, in response, displaying in the second level GUI screen an indication of acceptable ambient light;
  D) responsive to receiving the selecting, via the alignment process selection cell, of the eye alignment process, performing steps comprising:
    1) determining an alignment of the subject's eye to the computer controlled lensing system and displaying an indicator of said alignment in the alignment indicator field, and
    2) repeating (D)(1) until detecting the alignment meets an alignment condition;
  E) responsive to the detecting said state of alignment meets the alignment condition:
    1) displaying in the GUI second level screen an indication of a PLR measurement ready state, and correspondingly enabling the selection of the PLR measuring process, and
    2) responsive to receiving in the measurement process selection cell the selection of the PLR measuring process, displaying in the second level GUI screen an indication of an active PLR measurement testing, and controlling:
      a) an emitting from the pulsed illumination source of PLR stimulation pulses toward the subject's eye,
      b) a corresponding temporal measuring of a diameter of the subject's pupil, and
      c) a storing in the computer-readable storage medium of a corresponding PLR measurement record;
  F) based at least in part on a detecting a completion of step (E), reversing on the hardware display from displaying the second level GUI screen to displaying the first level GUI screen;
  G) responsive to receiving, via the process menu second cell, the selecting of the test results process, opening on the hardware display from the first level GUI screen to a third level GUI screen, and displaying in the third level GUI screen a third level selection cell, which is configured for selecting a PLR scoring, classification, and displaying process;
  H) responsive to receiving, via the third level selection cell, the selecting of the PLR scoring, classification, and displaying process, performing steps comprising:
    1) retrieving the PLR measurement record from the compute r-readable storage medium,
    2) accessing, based at least in part on the step (B) age-gender information, a comparative age-gender typical PLR data,
    3) based on the PLR measurement record, coding a PLR metric data for the subject, comprising a latency to constriction value, a return to baseline (RTB) value, and a combined total metric, wherein coding the combined total metric comprises a scaling based on a time threshold,
    4) determining, based at least in part on a scaling of the PLR metric data against the comparative age-gender typical PLR data, between a positive pupillary response (PPR) and negative pupillary response (NPR),
    5) generating a real-time Autism Pupillary (APS) score, by steps comprising: a) accessing a comparative growth curve associated with pupillary responses for metrics in accordance with age, and b) aligning a result of the step (H)(4) determining between PPR and NPR to the comparative growth curve, and
    6) displaying in the GUI third level screen the result of the step (H)(4) determining between PPR and NPR, the real-time APS score, and a PLR response plotted above or below a time threshold.

2. The computer-based method of claim 1, wherein: step (E)(2) further comprises a sub-step c), which comprises determining whether the PLR measurement record meets a quality condition, and step (F) further comprises, responsive to a result of sub-step (E)(2)(c) being a determining that the PLR measurement record meets the quality condition, displaying in the second level GUI screen an indication of a testing completion, prior to the reversing on the hardware display from the second level GUI screen back to displaying the first level GUI screen.

3. The computer-based method of claim 1, wherein step (D) is a first eye step (D) and step (E) is a first eye step (E), PLR measurement record, for a first eye of the subject, the first eye being one among the subject's left eye and right eye; in sub-step (E)(2)(c) of the first eye step (E), the PLR measurement record is a first eye PLR measurement record, and the method further comprises performing a second eye step (D) and a second eye step (E), the second eye being the other among the subject's left eye and right eye, wherein, in sub-step (E)(2)(c) of the second eye step (E) the PLR measurement record is a second eye PLR measurement record.

\* \* \* \* \*